United States Patent [19]

Rebafka

[11] 4,206,126
[45] Jun. 3, 1980

[54] PREPARATION OF CYCLIC α,β-UNSATURATED ETHERS

[75] Inventor: Walter Rebafka, Eppelheim, Fed. Rep. of Germany

[73] Assignee: BASF Aktiengesellschaft, Fed. Rep. of Germany

[21] Appl. No.: 2,335

[22] Filed: Jan. 10, 1979

[30] Foreign Application Priority Data

Jan. 30, 1978 [DE] Fed. Rep. of Germany ....... 2803987

[51] Int. Cl.$^2$ .............................................. C07D 309/18
[52] U.S. Cl. .............................. 260/345.1; 260/346.11
[58] Field of Search .......................... 260/345.1, 346.11

[56] References Cited

U.S. PATENT DOCUMENTS

| 2,556,325 | 6/1951 | Fleechaire et al. | 260/346.11 |
| 3,639,669 | 2/1972 | Stapp et al. | 260/345.1 |
| 3,651,092 | 3/1972 | Stapp et al. | 260/345.1 |

FOREIGN PATENT DOCUMENTS 817929  7/1949  Fed. Rep. of Germany .
1248669 8/1967  Fed. Rep. of Germany .

OTHER PUBLICATIONS

Hubert et al., J. Chem. Soc., Perkin II, pp. 366–370, 1972.

Primary Examiner—Norman Morgenstern
Assistant Examiner—G. T. Breitenstein
Attorney, Agent, or Firm—Keil & Witherspoon

[57] ABSTRACT

Cyclic α,β-unsaturated ethers are prepared by isomerizing the corresponding β,γ-unsaturated ethers at from 50° to 250° C. in the presence of an iron carbonyl as the catalyst, and of a base.

4 Claims, No Drawings

PREPARATION OF CYCLIC α,β-UNSATURATED ETHERS

The present invention relates to a process for the preparation of cyclic α,β-unsaturated ethers by isomerizing the corresponding β,γ-unsaturated ethers.

German Patent No. 1,248,669 describes a process for the preparation of 2,3-dihydrofurans, in which the corresponding 2,5-dihydrofurans are treated with a palladium, platinum, cobalt, ruthenium or nickel catalyst at from 60° to 170° C. According to a process described in U.S. Pat. No. 3,651,092, this isomerization is carried out with a nickel-arsenic catalyst. Both processes have the disadvantage that in some cases they give substantial amounts of by-products. If attempts are made to keep the proportion of these undesirable constituents low, then this can only be achieved by accepting lower conversions.

It has also been disclosed that the isomerization of dihydro-2,5-furans to dihydro-2,3-furans can be effected by heating in the presence of an alkali metal alcoholate. This process, disclosed in German Pat. No. 817,921, is economically of limited interest because of the difficulties entailed in separating off the amounts of alkali metal alcoholate which must be used. Furthermore, the process requires reaction times of up to 12 hours.

Further, it is known from J. Chem. Soc. Perkin II, 1972, 366 that 2,3-dihydrofuran can be prepared from 2,5-dihydrofuran by irradiation in the presence of an iron carbonyl. This process is very expensive because of the large amount of catalyst, the irradiation equipment required, and the long reaction time.

I have found that cyclic α,β-unsaturated ethers can be prepared particularly advantageously by isomerizing the corresponding β,γ-unsaturated ethers with an iron carbonyl as the catalyst, if the isomerization is carried out at from 50° to 250° C. and in the presence of a base.

The process according to the invention gives the α,β-unsaturated ethers smoothly and in high yields. This advantageous result is surprising since on the one hand it was known from J. Chem. Soc. Perkin II, 1972, 367 that a thermal treatment of β,γ-unsaturated cyclic ethers in the presence of iron pentacarbonyl, but without irradiation, results, even with lengthy reaction times, in only minimal isomerization of the double bond, whilst on the other hand, in agreement with the statements in German Patent 817,921, page 1, lines 23-26, isomerization of the β,γ-unsaturated cyclic ethers does not occur on heating in aqueous alkali.

The cyclic β,γ-unsaturated ethers which may be used as starting materials are, for example, 2,5-dihydrofurans and 5,6-dihydropyrans of the formulae

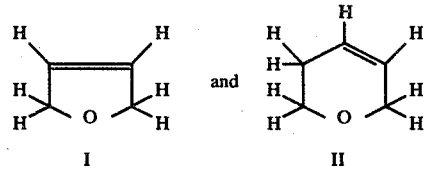

I  II where the hydrogen atoms may be replaced by alkyl or alkylene of 1 to 10, preferably 1 to 4, carbon atoms. On isomerization in accordance with the invention, the starting materials of the formulae I and II are converted to the compounds of the formulae

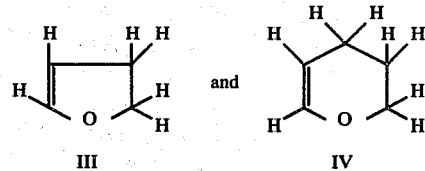

III  IV where the hydrogen atoms may correspondingly be replaced by the said alkyl or alkylene groups.

Amongst the substituted 2,5-dihydrofurans of the formula I, preferred starting materials are those where from 1 to 4 H atoms are substituted by alkyl, especially by methyl or ethyl. Examples of such dihydrofuran derivatives are 2,5-dihydrofuran, 2,2,5-trimethyl-2,5-dihydrofuran, 2,5-dimethyl-2,5-dihydrofuran and 5-methyl-2,5-dihydrofuran.

Amonst the substituted 5,6-dihydropyrans of the formula II, preferred starting materials are those where from 1 to 4H atoms are substituted by alkyl, especially by methyl or ethyl. Examples of such pyran derivatives are 5,6-dihydro-2-[H]-pyran, 2-methyl-5,6-dihydro-2-[H]-pyran, 4-methyl-5,6-dihydro-2-[H]-pyran and 2,4-dimethyl-5,6-dihydro-2-[H]-pyran.

The iron carbonyl used is preferably iron pentacarbonyl. The base used is an inorganic base, for example an alkali metal hydroxide or alkaline earth metal hydroxide, eg. the hydroxides of potassium, sodium, barium, or calcium, or organic bases, eg. trimethylamine, tributylamine, ethylamine or urotropine. Potassium hydroxide and sodium hydroxide are industrially of particular interest. The base may be used without a solvent or as a solution in a solvent, for example water.

The isomerization according to the invention is carried out at from 50° to 250° C., preferably from 130° to 200° C., continuously or batchwise. The iron carbonyl is used in an amount of from 0.01 to 5% by weight, preferably from 0.1 to 2% by weight, and the base in an amount of from 0.01 to 5% by weight, preferably from 0.05 to 2% by weight, in each case based on the compound to be isomerized.

The isomerization can also be carried out in organic solvents which are inert under the reaction conditions, for example ethers, eg. diethyl ether, dioxane or tetrahydrofuran, alkanols, eg. ethanol or isobutanol, aromatic or aliphatic hydrocarbons, eg. heptane or toluene, or mixtures of these solvents, and, when using inorganic bases, also in water.

An example of a suitable procedure is to keep the starting material, the iron carbonyl and the base, with or without a solvent, at the reaction temperature for from 0.5 to 5 hours and then to isolate the end product in the conventional manner from the mixture, for example by fractional distillation.

The compounds obtainable by the process of the invention may for example be used as solvents or are valuable intermediates for the preparation of drugs and plastics.

EXAMPLE 1

3 parts of iron pentacarbonyl and 1.5 parts of powdered solid sodium hydroxide are added to 150 parts of 2,5-dihydrofuran. The mixture is kept at 180° C. for 5 hours and the volatiles are then distilled at 50°–55° C., leaving 4 parts of a residue. According to a gas chromatogram, the distillate contains 96% of 2,3-dihydrofuran and 1.6% of 2,5-dihydrofuran. The yield is 90%.

EXAMPLE 2

1,200 parts of 2,5-dihydrofuran, 12 parts of powdered sodium hydroxide and 24 parts of iron pentacarbonyl are heated at 145° C. for 1 hour. The reaction product contains 90.8% of 2,3-dihydrofuran and 6.8% of 2,5-dihydrofuran. The yield of 2,3-dihydrofuran is 85%.

EXAMPLE 3

A mixture of 150 parts of 2,5-dihydrofuran, 3 parts of iron pentacarbonyl and 1.5 parts of 50% strength aqueous sodium hydroxide solution is kept at 160° C. for 5 hours. The reaction product is freed from the residue (3 parts) by distillation. The distillate contains 93% of 2,3-dihydrofuran and 5% of 2,5-dihydrofuran. The yield of 2,3-dihydrofuran is 90%.

EXAMPLE 4

A mixture of 2,000 parts of 4-methyl-5,6-dihydro-2[H]-pyran, 40 parts of iron pentacarbonyl and 40 parts of sodium hydroxide powder is kept at 180° C. for 5 hours. The reaction product, freed from the residue (100 parts) by distillation, contains 63% of 4-methyl-2,3-dihydro-4[H]-pyran, the remainder being unconverted starting material. The two components can easily be separated by rectification. The yield is 90%, based on 4-methyl-5,6-dihydro-2[H]-pyran converted.

EXAMPLE 5

500 g of 2,5-dihydrofuran, 10 g of iron pentacarbonyl and 10 g of 50% strength sodium hydroxide solution are together rectified in a batch-operated 1 m laboratory column under atmospheric pressure, using a reflux ratio of 10:1. 395 g of a distillate, which contains 95% of 2,3-dihydrofuran (yield 75%) pass over at 53°–55° C.

I claim:

1. A process for the preparation of a cyclic alpha, beta-unsaturated ether by isomerizing a corresponding substituted or unsubstituted 2,5-dihydrofuran or a substituted or unsubstituted 5,6-dihydropyran with iron pentacarbonyl as the catalyst, wherein the isomerization is carried out at from 50° to 250° C. in the presence of a base selected from the group consisting of an alkali metal hydroxide, alkaline earth metal hydroxide and an organic amine.

2. The process of claim 1, wherein the iron penta carbonyl is used in an amount of from 0.05 to 5% by weight, preferably from 0.5 to 2% by weight, based on the starting material.

3. The process of claim 1, wherein the base is used in an amount of from 0.01 to 5% by weight, preferably from 0.5 to 2% by weight, based on the starting material.

4. The process of claim 1, wherein an alkali metal hydroxide or alkaline earth metal hydroxide is used as the base.

* * * * *

UNITED STATES PATENT AND TRADEMARK OFFICE
CERTIFICATE OF CORRECTION

PATENT NO. : 4,206,126

DATED : June 3, 1980

INVENTOR(S) : Walter Rebafka

It is certified that error appears in the above—identified patent and that said Letters Patent is hereby corrected as shown below:

On the first page, the first Foreign Patent Document cited reads "817929  7/1949  Fed. Rep. of Germany".

It should read "817921  7/1949  Fed. Rep. of Germany".

*Signed and Sealed this*

*Ninth* Day of *December 1980*

[SEAL]

*Attest:*

SIDNEY A. DIAMOND

*Attesting Officer*

*Commissioner of Patents and Trademarks*